United States Patent
Yang et al.

(10) Patent No.: US 12,121,552 B2
(45) Date of Patent: *Oct. 22, 2024

(54) *Pseudomonas chlororaphis* SPECIES AND ITS USE IN THE CONTROL OF FISH DISEASES CAUSED BY BACTERIA AND FUNGI

(71) Applicants: T3 Bioscience, Inc., Mequon, WI (US); UWM RESEARCH FOUNDATION, INC., Milwaukee, WI (US)

(72) Inventors: Ching-Hong Yang, Mequon, WI (US); Jian Huang, Milwaukee, WI (US)

(73) Assignees: T3 BIOSCIENCE, INC., Mequon, WI (US); UWM RESEARCH FOUNDATION, INC., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/120,528

(22) Filed: Mar. 13, 2023

(65) Prior Publication Data
US 2023/0285472 A1 Sep. 14, 2023

Related U.S. Application Data

(60) Provisional application No. 63/319,429, filed on Mar. 14, 2022.

(51) Int. Cl.
*A61K 35/74* (2015.01)
*A61K 31/05* (2006.01)
*A61P 31/04* (2006.01)

(52) U.S. Cl.
CPC .............. *A61K 35/74* (2013.01); *A61K 31/05* (2013.01); *A61P 31/04* (2018.01)

(58) Field of Classification Search
CPC .......... A61K 35/74; A61K 31/05; A61P 31/04
See application file for complete search history.

(56) References Cited

U.S. PATENT DOCUMENTS

| | | |
|---|---|---|
| 2022/0000232 A1 | 1/2022 | Kelsch et al. |
| 2022/0104487 A1 | 4/2022 | Yang |
| 2022/0104500 A1 | 4/2022 | Yang |
| 2022/0105080 A1 | 4/2022 | Yang |
| 2022/0232834 A1* | 7/2022 | Yang .......................... A01P 3/00 |

FOREIGN PATENT DOCUMENTS

WO    WO-2020246609 A1 * 12/2020 ............. A01K 61/13

OTHER PUBLICATIONS

Peix et al. "Reclassification of Pseudomonas aurantiaca as a synonym of Pseudomonas chlororaphis and proposal of three subspecies . . . " 2007, International Journal of Systematic and Evolutionary Microbiology 57(6):1286-1290. (Abstract and p. 1286) (Year: 2007).*
Li et al. "Semi-synthesis of antibacterial dialkylresorcinol derivatives." 2021, Journal of Antibiotics 74, 70-75, first published online Aug. 2020 (entire document) (Year: 2020).*
Li, J., Shi, Y. & Clark, B.R. (2020). "Semi-synthesis of antibacterial dialkylresorcinol derivatives." Journal of Antibiotics 74, 70-75.
Piex A., Valverde, A., Rivas, R., Igual, J.M., Ramirez-Bahena M-H., Mateos P.F., Santa-Regina I., Rodriguez-Burrueco C., Martinez-Molina E., & Velaquez E. (2007). "Reclassification of Pseudomonas aurantiaca as a synonym of *Pseudomonas chlororaphis* and proposal of three subspecies, *P. chlororaphis* subsp. *chlororaphis* subsp. nov., *P. chlororaphis* subsp. *aureofaciens* subsp. nov., comb. nov. and *P. chlororaphis* subsp. *aurantiaca* subsp. nov., comb. nov." International Journal of Systematic and Evolutionary Microbiology 57(6): 1286-1290.
International Search Report and Written Opinion, Jul. 23, 2023.
Girard L, Lood C, Rokni-Zadeh H, van Noort V, Lavigne R, De Mot R. "Reliable Identification of Environmental Pseudomonas Isolates Using the rpoD Gene." Microorganisms. Jul. 31, 2020;8(8): 1166. doi: 10.3390/microorganisms8081166. PMID: 32752051; PMCID: PMC7463772.
García-Valdés, Elena and Jorge Lalucat. "Pseudomonas : Molecular Phylogeny and Current Taxonomy." (2016). In: Pseudomonas: Molecular and Applied Biology, R.S. Kahlon (ed.), (Springer International Publishing (Switzerland)).
Peix, Alvaro; Ramírez-Bahena, Martha-Helena; and Velazquez Encarna, "The current status on the taxonomy of Pseudomonas revisited: An update." Infection, Genetics and Evolution, 57:106-116 (2018).
Shi et al. "Isolation, identification, and decomposition of antibacterial dialkylresorcinols from a Chinese Pseudomonas aurantiaca strain." J. Nat. Prod. 83.2 (2020): 194-201.
Deng, P. Mississippi State University Doctoral Thesis "Genetic Characterization of Antimicrobial Activities of the Bacteria Burkholderia Contaminans MS14 and PseudomonasBacteria Burkholderia Contaminans MS14 and Pseudomonas Chlororaphis UFB2Chlororaphis UFB2" (May 7, 2016).

\* cited by examiner

*Primary Examiner* — Terry A McKelvey
*Assistant Examiner* — Andrew T Moehlman
(74) *Attorney, Agent, or Firm* — Klintworth & Rozenblat IP LLP

(57) ABSTRACT

The present invention relates to an antimicrobial composition and probiotics against bacterial and fungal pathogens of fish. In particular, the invention pertains to a novel strain of the bacterial species *Pseudomonas chlororaphis* subsp. *aurantiaca* 1214-CHY4 (ATCC accession number PTA-126941), the cells, cell broth, and novel metabolites produced from the bacterial strain that can inhibit the growth of a variety of fish pathogens.

11 Claims, 1 Drawing Sheet

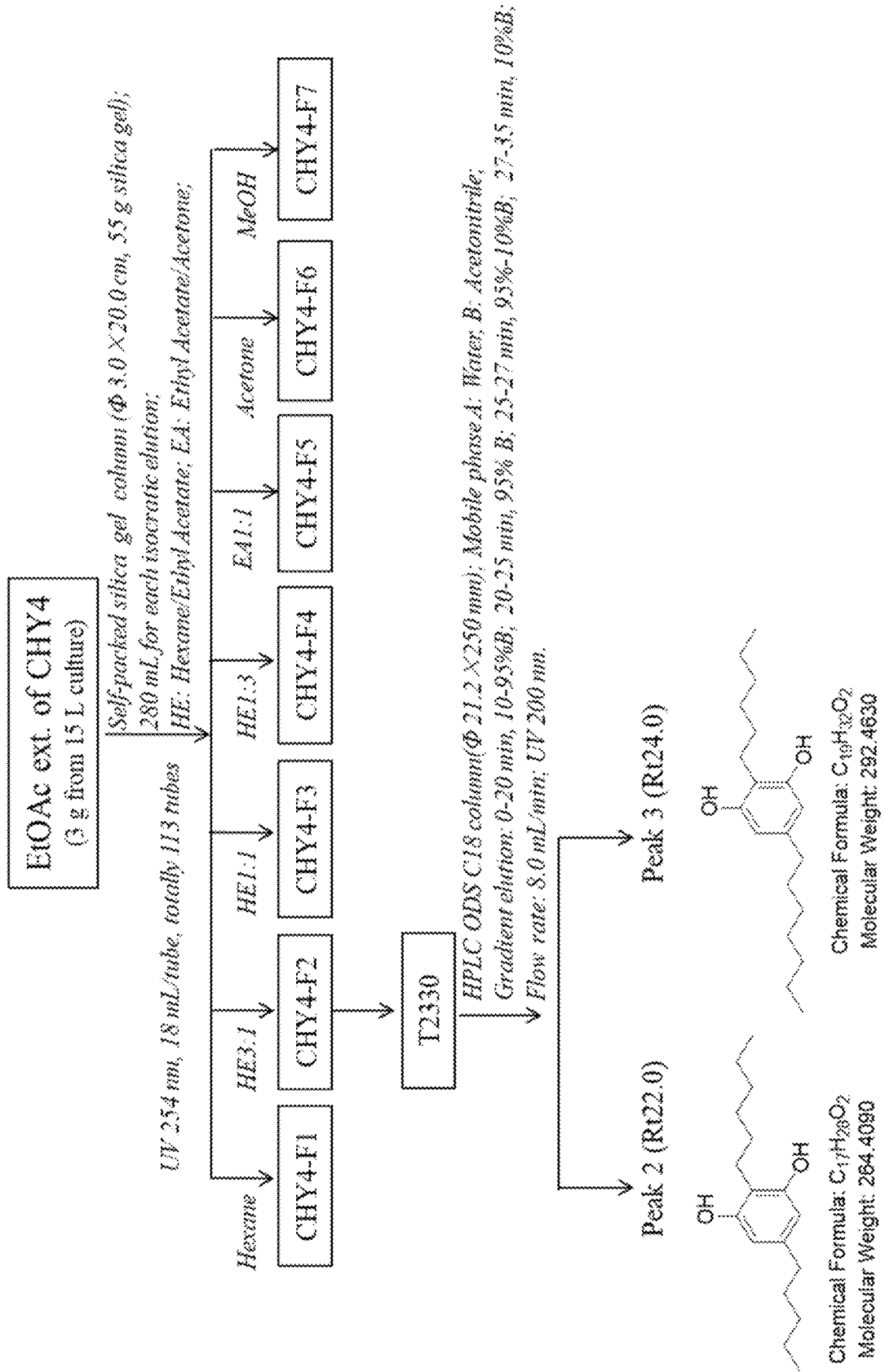

Pseudomonas chlororaphis SPECIES AND ITS USE IN THE CONTROL OF FISH DISEASES CAUSED BY BACTERIA AND FUNGI

CROSS-REFERENCE TO RELATED APPLICATIONS

This application claims benefit of priority to U.S. Provisional Patent Application Ser. No. 63/319,429, filed Mar. 14, 2022 and entitled "*PSEUDOMONAS CHLORORAPHIS* SPECIES AND ITS USE IN THE CONTROL OF FISH DISEASES CAUSED BY BACTERIA AND FUNGI," the contents of which are herein incorporated by reference in its entirety.

BACKGROUND OF THE INVENTION

*Aeromonas salmonicida* is a Gram-negative, facultative anaerobic, nonmotile bacterium responsible for causing furunculosis in salmonid populations and other species (Gauthier et al., 2021). *A. salmonicida* is a prime virulent bacterium due to its ability to infect a variety of hosts, multiply, and adapt (Charette et al., 2021). Furunculosis causes muscle lesions, sepsis, inflammation, hemorrhages, and death in freshwater fish populations. Spawning and smolting fish species are major victims of furunculosis. Poor water quality is the main reason for contamination; however, it can also be impacted by stresses such as high temperature, trauma, and overcrowding (Gauthier et al., 2021; Charette et al., 2021). Furunculosis costs Canadian aquaculture industry over $40 million annually, accounting for approximately 10% in total annual losses of infectious diseases (Nash et al., 2006). Antibiotic sulfamethazine has been used to control furunculosis in rainbow trout, brook trout, and brown trout at a rate of 200 mg of drug per kilogram of fish per day for 14 days. Sulfisoxazole (Gantrisin) was applied to treat brown trout, preferentially. Oxytetracycline (Terramycin®, Pfizer, Inc.) was used for all species of salmonids at a dose of 50 to 80 mg of drug per kilogram of fish per day for 10 days. ROMET® (Hoffman-LaRoche, Inc.), a complex with sulfadimethoxine and ormetoprim at a ratio of 5:1, treated furunculosis at the rate of 50 mg per kilogram of fish per day for 14 days (Bebak-Williams and Bullock, 2002). Vaccines formulated with mineral oil adjuvants have been used to induce protection (Midtlyng et al., 1996; Bebak-Williams and Bullock., 2002; Romer Villumsen et al., 2012; Gudding et al., 2013; Villumsen et al., 2015). However, a variety of side effects have been observed, including adhesions and pigmentation of the peritoneal viscera, low growth rate, deformed vertebrae, autoimmunity, and hypergammaglobulinemia (Midtlyng et al., 1996; Villumsen et al., 2015; Berg et al., 2006; Satoh et al., 2011; Koppang et al., 2008).

Two Gram-positive bacterial species, *Streptococcus agalactiae* and *Streptococcus iniae*, also cause severe impact to the aquaculture industry. *S. agalactiae* causes meningitis in fish, and infected survival often shows neurological disorders, such as constant, aberrant swimming. *S. agalactiae* has become a major pathogen for tilapia. Freshwater and saltwater fish are susceptible to infection by *S. iniae*. *S. iniae* causes meningoencephalitis, skin lesions, and septicemia. *S. iniae* infections have been reported in at least 27 species of cultured or wild fish, resulting in over US$100M in annual losses. *S. iniae* can cause disease in mammals, including humans. A few antibiotics have been applied successfully to control *S. iniae* infection in fish, including enrofloxacin, amoxicillin, erythromycin, furazolidone, and oxytetracycline. As a quinolone antibiotic, enrofloxacin has been effectively used to treat hybrid striped bass (*Morone chrysops×M. saxatilis*). However, a resistant strain was developed during the trial (Stoffregen et al., 1996). Antibiotics have been ineffective for various reasons, particularly the occurrence of drug resistance (Park et al., 2009; Mishra et al., 2018). For *S. agalactiae*, erythromycin has been proved effective in the field by feeding at a rate of 1.5 grams per pound of food for 10 to 14 days. Amoxicillin has also shown its potency to control infected tilapia and sunshine bass at a rate of 3.6 grams per pound of food for 8 to 12 days (Darwish and Ismaiel 2003; Darwish and Hobbs 2005). Vaccination against *S. iniae* has been tried but limited success was achieved (Agnew et al., 2007). AQUAVAC® Strep Sa-Si (MSD Animal Health, Merck & Co., Inc.) is a commercial bivalent oil-adjuvant vaccine launched in 2019 that protects against both *Streptococcus agalactiae* (serotype Ia, Ib and III) and *Streptococcus iniae* infections in tilapia (*Oreochromis* sp.) and other susceptible fish species to reduce mortality. A culture *Aeromonas sobria* GC2 showed potency to prevent the clinical disease caused by *Streptococcus iniae* (Brunt et al., 2005).

Vibriosis, caused by *Vibrio* spp., is considered the most prevalent in the aquaculture industry, with mass mortality and great economic loss. Among the *Vibrio* species, *Vibrio parahaemolyticus* causes acute hepatopancreas necrosis disease in squids, mackerels, tunas, sardines, crabs, conchs, shrimps, bivalves, and ornamental fishes. Particularly, this bacterium causes gastrointestinal illness in humans via the consumption of raw or undercooked seafood. The *Vibrio* infected fishes show common symptoms, including dark skin, pale gills, exophthalmia, skin ulcers, corneal opacity, splenomegaly, enteritis, and haemorrhages at the base of fins, especially tail and fin rot (Toranzo et al., 2005). Outbreaks of acute hepatopancreatic necrosis disease (AHPND) caused by *Vibrio* species directly or indirectly cost over US$44 billion from 2010 to 2016 globally (Tang et al., 2019). A study indicated that *V. parahaemolyticus* isolated from grouper samples in Malaysia was susceptible to tetracycline, streptomycin, erythromycin, and bacitracin, but resistant to ampicillin, penicillin G, and vancomycin (Amalina et al., 2019). The *V. parahaemolyticus* cells were sonicated and the supernatant (lysate) was used as the vaccine against the infection of *V. parahaemolyticus* (Reyes-Becerril et al., 2017). *Bacillus licheniformis* Dahb1 was used as a probiotic strain on the Asian catfish, *Pangasius hypophthalmus* against *V. parahaemolyticus* Dahv2. *B. licheniformis* Dahb1 was orally fed to the fish and achieved 100% relative percent survival (RPS) compared to 40% of RPS with controls (Gobi et al., 2016).

*Piscirickettsia salmonis* is the bacterial causative agent of piscirickettsiosis (Fryer and Hedrick, 2003). Piscirickettsiosis is also recognized as salmon *rickettsia* syndrome and salmonid rickettsial septicaemia (SRS) (Rozas and Enriquez, 2014). *P. salmonis* primely infects various salmonid hosts but also several non-salmonid hosts such as the white seabass (*Atractoscion nobilis*), Patagonian blenny (*Eleginops maclovinus*), Cape redfish (*Sebastes capensis*), tadpole codling (*Salilota australis*), and European seabass (*Dicentrarchus labrax*) (Bartholomew et al., 2017). The infection induces multifocal, necrotic areas of internal organs such as the liver, kidney, intestine, skeletal muscle, and spleen (Toranzo et al., 2005), and causes mortality rates up to 90% in some salmon populations (Bravo and Campos, 1989; Sernapesca, 2015). Economic losses caused by *P. salmonis* have been over US $450 million in 2012 (Camussetti et al., 2015). Antibiotics have been extensively used to control SRS (Cabello et al. 2013). In 2014, 90% of antibiotics applied in Chilean aquaculture were used to treat piscirickettsiosis (Henríquez et al., 2016). Initially, quinolones (flumequine, oxolinic acid) were selected but were later replaced due to food safety and environmental protection (Miranda et al., 2013). Currently, florfenicol (FFC) and oxytetracycline (OTC) represent 82.5% and 16.8% of antibiotic usage for *P. salmonis* treatment. During 2016, Chilean companies utilized approximately 0.53 kg of antibiotics per ton of harvested salmon, representing one of the highest rates internationally of antibiotic consumption per ton of harvested fish (Mirinda et al. 2018). In this situation, a high dosage of antibiotics enters the marine environment that raises possibly negative ecological and environmental consequences and potential risks for human health. Actually, *P. salmonis* has demonstrated a sign of resistance to both FFC and OTC from a comprehensive antibiotic susceptibility study (Henríquez et al., 2016). The first commercial vaccine against SRS was released to the market in 1999 and then more than 50% of the salmon in Chile was vaccinated. However, the vaccination ratio of the salmon had decreased to 17% by 2003, suggesting that the protection of this vaccine did not meet the demand of the market (Bravo and Midtlyng, 2007).

*Renibacterium salmoninarum* is a Gram-positive, causative agent of "bacterial kidney disease" (BKD) in salmonid fish (Toranzo et al. 1990; Sakai and Kobayashi 1992; Fryer and Lannan 1993). BKD is a severe systemic infectious disease, causing necrosis and granulomatous inflammation on the internal organs. BKD can cause high mortality as high as 80% in Pacific salmon (*Oncorhynchus* spp.) and 40% in Atlantic salmon among juvenile fish and has been proposed as the limiting factor in salmon species in western North America (Flagg et al. 1995). The outbreak of BKD in 2015 at Glenwood Spring, Colorado cost Colorado Park & Wildlife (CPW) over $1.2 million with loss of near 70,000 sub-catchable and catchable trout and affected fish stocking statewide for several years (Kowalski et al., 2018). Sulfadiazine (264 mg/kg) was the first antibiotic against *R. salmoninarum* in Blueback salmon (*Oncorhynchus nerka*) in 1951 (Rucker et al. 1951). Since then, other antibiotics were selected to treat BKD. Azithromycin (30 mg/kg fish for 14 days) and erythromycin (100 mg/kg fish for 28 days) have been used in Fall Chinook salmon (*Oncorhynchus tshawytscha*) (Fairgrieve et al. 2005). Baytril®, commercialized enrofloxacin by the Bayer company, was applied in rainbow trout (*Oncorhynchus mykiss*) by 1.25-2.5 mg/kg for 10 days to decrease the mortality significantly (Hsu et al. 1994; Austin and Austin, 2016). It is important to note that antibiotic resistance of *R. salmoninarum* have been reported (Elliott et al. 1989; Wiens et al. 2011). Attempts have been made to develop whole-cell inactivated bacteria as bacterin-killed vaccines against BKD (Eslamloo et al. 2020). Current vaccines cannot provide reliable protection against BKD.

*Flavobacterium columnare* and F. psychrophilumis are thin Gram-negative rod bacteria and the causative agent of *columnaris*, bacterial cold water disease, and rainbow trout fry syndrome disease. *Columnaris* is the second leading cause of mortality in channel catfish farming (Durborrow et al. 1988). F. psychrophilumis affects salmonids primarily, but also eels, carps, perches, and many others. In *F. columnare*, the infection is often initiated externally on the body surface, fins or gills, and subsequently developed into yellow-orange lesions to encircle the fish along the dorsal midline, resembling a "saddleback" (Bullock et al., 1986; Plumb, 1999). Mortalities in extreme cases have reached up to 90% for channel catfish, and mortalities reached 50-60% in commercial ponds, resulting in USD 30 million in economic losses for the U.S. catfish industry (Plumb and Hanson, 2011; Shoemaker et al., 2011; Zhou et al., 2018). In the early stages of *columnaris* disease, some antibiotics have been effectively used in bath therapies, including chloramphenicol, nifurpirinol, nifurprazine, and oxolinic acid. If the disease develops to an advanced stage and/or signs of septicaemia are observed, fishes normally were treated by orally feeding. Oxytetracycline, sulfonamides, (sulfamerazine and sulfamethazine), nitrofuran, and florfenicol have been used orally with a varied efficacy (Declercq et., 2013). Concerns also have been raised due to the overuse of the antibiotics, including possible allergic reactions and the emergence of drug-resistant bacteria (Serrano, 2005). Attempts have been made to develop effective *columnaris* vaccines. Formalin-killed whole-cell vaccines provided limited protection by immersion. A few live-attenuated vaccines were commercialized, including Fryvacc 1, Fryvacc 2, and AQUAVAC-COL vaccine (Zhou et al., 2018). The application of the vaccines by the catfish industry declined due to variable efficacy under field conditions (Bebak et al., 2012; Wise et al., 2021). Two *Pseudomonas fluorescens* were isolated from the skin and gut of healthy Walleye (*Sander vitreus*) and showed an inhibitory effect on the growth of *F. columnare* in vitro and in vivo (Seghouani et al., 2017).

The filamentous organism *Tenacibaculum maritimum* is the aetiological agent of marine tenacibaculosis, which affects a large number of marine fish species in the world and causes tremendous economic loss to the aquaculture industry (Avendaño-Herrera et al., 2006). In British Columbia (BC), the outbreak of tenacibaculosis cost $3.8 million to the local industry (Powell and Podlasly, 2015). Tenacibaculosis causes gross lesions on the body surface of teleosts, including ulcerative skin lesions, necrosis of skin, fin, eroded mouth, frayed fins, gill rot, and tail rot (Toranzo et al., 2005; Florio et al., 2016). Both laboratory and field trials demonstrated amoxycillin and trimethoprim are effective in Atlantic salmon and rainbow trout against *Tenacibaculum maritimum* (Soltani et al., 1995). Oxytetracycline in salmonids (Navarrete et al., 2008) and furazolidone in turbot (Alsina and Blanch, 1993) were also effective in controlling the disease. Tetracycline, enrofloxacin, flumequine, and potentiated sulfonamides have been used to treat turbot and sole cultures. Among them, enrofloxacin showed its highest efficacy in controlling *Tenacibaculum maritimum* outbreaks. However, resistant strains have been reported (Avendaño-Herrera, 2005). Several vaccine formulations have been tested against *Tenacibaculum maritimum*. A vaccination trial for Atlantic salmon in Tasmania showed that only vaccine with adjuvant achieved relative percent survival (RPS) values of 79.6% and 78% compared to Control and IP Control, respectively (van Gelderen et al., 2009). A vaccine has been patented for turbot and gave up to 85% protection buy only to turbot (Toranzo et al., 2005). Recently, formalin-inactivated whole-cell vaccines for *T. maritimum* in Atlantic salmon smolts were investigated. Although the whole-cell oil-adjuvanted vaccines induced an antibody response, vaccines did not provide protection for the fish (Frisch et al., 2018). A commercial vaccine (ICTHIOVAC) against tenacibaculosis derived from inactivated bacteria is now available. It claims a protection ≥75% and lasts for 6 months, but it still lacks the support from scientific literature (Miccoli et al., 2019).

BRIEF SUMMARY OF THE INVENTION

In a first aspect, a method of controlling a fish pathogen and associated disease of a fish is provided. The method includes several steps. One step includes producing an aquacultural composition comprising Formula (I), Formula (II), or a combination thereof:

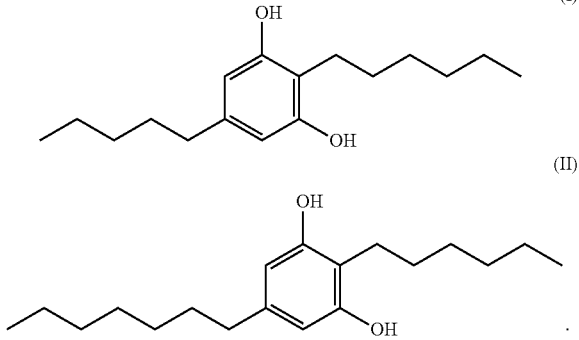

Another step includes applying said aquacultural composition to the fish to inhibit the growth of the fish pathogen and the associated disease on the fish.

In a second aspect, a method of controlling a fish pathogen disease is provided. The method includes the step of applying an aquacultural composition comprising between about $1.0 \times 10^5$ and $1.0 \times 10^9$ cfu per mL or $1.0 \times 10^5$ and $1.0 \times 10^9$ cfu per gram with a carrier of *P. chlororaphis* subsp. *aurantiaca* 1214-CHY4 (ATCC Accession No. PTA-126941) to fish to inhibit the growth of a fish pathogen and an associated disease.

BRIEF DESCRIPTION OF THE DRAWINGS

FIG. 1 illustrates an exemplary scheme for isolation and purification of Peaks 2 and 3.

DETAILED DESCRIPTION

The present invention relates to novel metabolites produced by 1214-CHY4 strain listed in this patent that exhibits antimicrobial activity against pathogenic microorganisms, including bacteria and fungi. From the 16S rRNA and other housekeeping gene sequences, the strain was identified as *Pseudomonas chlororaphis* subsp. *aurantiaca* 1214-CHY4. The cell broth of the 1214-CHY4 shows good potency to multiple fish and aquatic pathogens. The cell broth of the 1214-CHY4 contains two novel, potent natural products, which are designated as Peak 2 and Peak 3 (Formula (I) and Formula (II)), as depicted below

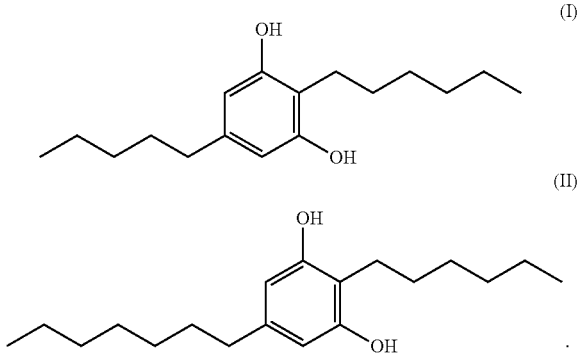

These compounds, their method of production and applications for inhibiting fish microbial pathogens is disclosed in greater detail herein.

Definitions

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

The terms "probiotics" and "probiotic organism" refer to a live, dead or component of a microbial cell, which is administered via the feed or to the rearing water, benefiting the host by improving disease resistance, health status, growth performance, feed utilization, stress response, general vigor, or reducing the pest's population or abundance in the environment, which is achieved at least in part via improving the hosts-microbial balance or the microbial balance of the ambient environment. (Hoseinifar et al., 2018; Soliman et al., 2019).

The compounds referred to as Peak 2 and Peak 3 corresponds to chemical compounds having the Formula (I) and Formula (II), respectively, as illustrated below:

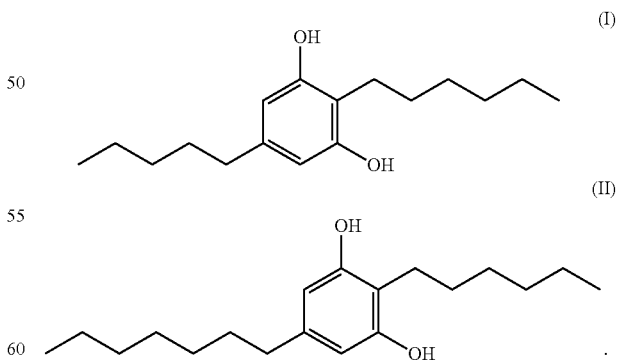

In a first aspect, a method of controlling a fish pathogen and associated disease of a fish is provided. The method includes several steps. One step includes producing an aquacultural composition comprising Formula (I), Formula (II), or a combination thereof:

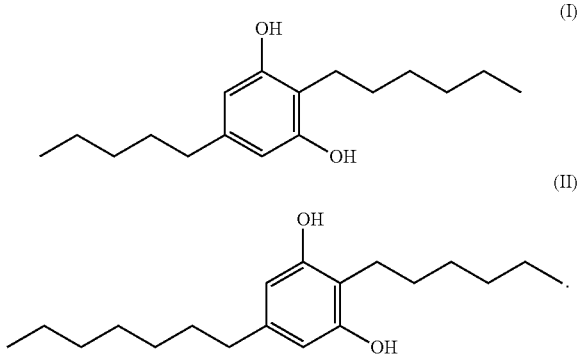

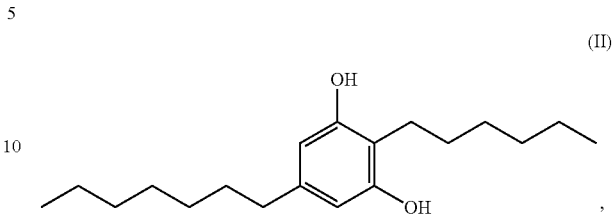

or a combination thereof.

In a third respect, the composition comprising between about $5.0 \times 10^7$ and $2.0 \times 10^8$ cfu per mL or about $5.0 \times 10^7$ and $2.0 \times 10^8$ cfu per gram with a carrier of *P. chlororaphis* subsp. *aurantiaca* 1214-CHY4 (ATCC Accession No. PTA-126941).

In a fourth respect, the fish pathogen is selected from the group consisting of *Streptococcus agalactiae*, *Streptococcus iniae*, *Renibacterium salmoninarum*, *Aeromonas salmonicida*, *Tenacibaculum maritimum*, *Vibrio parahaemolyticus*, *Piscirickettsia salmonis*, *Flavobacterium psychrophilum* and *Flavobacterium columnare*.

In a fifth respect, the associated disease is selected from the group consisting of streptococcosis, bacterial kidney disease, furunculosis, tenacibaculosis, vibriosis (acute hepatopancreatic necrosis disease), piscirickettsiosis, and *columnaris* diseases.

In a sixth respect, the fish is selected from the group consisting of Salmonids, trout, cyprinids, pikes, perches, bullheads, turbots, halibuts, catfish, goldfish, eels, tilapia, carps, freshwater aquarium fish, fresh-water fish, sea-water fish, wild fish, farm fish, fish, shrimps, squids, oysters, crabs, and conchs.

Biological Deposit Information

One of the inventors, Dr. Ching-Hong Yang (residing at 10120 N. Sheridan Dr., Mequon, WI 53902, US), acting on behalf of Applicants, submitted the bacterial strain *Pseudomonas chlororaphis* subsp. *aurantiaca* 1214-CHY4 to the American Type Culture Collection (ATCC®), P.O. Box 1549, Manassas, VA 20110 USA ("ATCC Patent Depository") on Dec. 22, 2020, as evidenced by the Form PCT/RO/134, "Indications Relating to Deposited Microorganism," pursuant to PCT Rule 13bis (filed with this application). Following viability testing, the ATCC Patent Depository accorded this deposited bacterial strain the following Accession number, effective Dec. 22, 2020: *Pseudomonas chlororaphis* subsp. *aureofaciens* (now *aurantiaca*) 1214-CHY4 (Accession No. PTA-126941). Dr. Yang grants permission to Applicants to include this biological deposit disclosure in the present application and gives his unreserved and irrevocable consent to it being made available to the public as of the date of filing.

Another step includes applying said aquacultural composition to the fish to inhibit the growth of the fish pathogen and the associated disease on the fish.

In a first respect, fish pathogen is selected from the group consisting of *Streptococcus agalactiae*, *Streptococcus iniae*, *Renibacterium salmoninarum*, *Aeromonas salmonicida*, *Tenacibaculum maritimum*, *Vibrio parahaemolyticus*, *Piscirickettsia salmonis*, *Flavobacterium psychrophilum* and *Flavobacterium columnare*.

In a second respect, the associated disease is selected from the group consisting of streptococcosis, bacterial kidney disease, furunculosis, tenacibaculosis, vibriosis (acute hepatopancreatic necrosis disease), piscirickettsiosis, and *columnaris* diseases.

In a third respect, the fish is selected from the group consisting of Salmonids, trout, cyprinids, pikes, perches, bullheads, turbots, halibuts, catfish, goldfish, eels, tilapia, carps, freshwater aquarium fish, fresh-water fish, sea-water fish, wild fish, farm fish, fish, shrimps, squids, oysters, crabs, and conchs.

In a second aspect, a method of controlling a fish pathogen disease is provided. The method includes the step of applying an aquacultural composition comprising between about $1.0 \times 10^5$ and $1.0 \times 10^9$ cfu per mL or $1.0 \times 10^5$ and $1.0 \times 10^9$ cfu per gram with a carrier of *P. chlororaphis* subsp. *aurantiaca* 1214-CHY4 (ATCC Accession No. PTA-126941) to fish to inhibit the growth of a fish pathogen and an associated disease.

In a first respect, applying an aquacultural composition to the fish is administered by a food-borne oral route, bioencapsulation, bath, dip, flush, injection, and topical application.

In a second respect, the aquacultural composition is selected from spent media or natural metabolites of *P. chlororaphis* subsp. *aurantiaca* 1214-CHY4 (ATCC Accession No. PTA-126941), a composition comprising of the Formula (I) isolated from *P. chlororaphis* subsp. *aurantiaca* 1214-CHY4 (ATCC Accession No. PTA-126941):

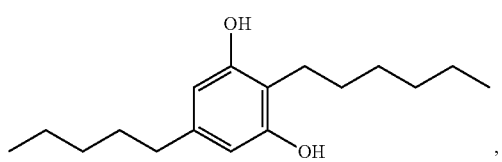

EXAMPLES

Example 1. Culture, Crude Extract Preparation, and Purification of Peak 2 and Peak 3

The strain *P. chlororaphis* subsp. *aurantiaca* 1214-CHY4 was streaked onto LB plate and cultivated in 28° C. incubator for one day. Several colonies were picked up and inoculated into YME medium in a fermenter for 3 days at 28° C. with an agitation speed at 200 rpm. The bacterial culture was extracted with an equal volume of ethyl acetate. Ethyl acetate was dried to obtain the crude extract. For purification of the Peak 2 and 3, the concentrated ethyl acetate extract solution was applied onto a Yamazen flash system (AI-580) equipped with a silica gel column (I.D. 3.0×20.0 cm, 55 g, 30μ, 60 Å) and separated by different concentrations of hexane/ethyl acetate (See FIG. 1). The fraction separated by hexane/ethyl acetate 3:1 (HE 3:1) was collected, dried, and then dissolved in methanol. HPLC purification was performed by using ODS C18 column (Φ21.2×250 mm) with mobile phase A: water, B: acetonitrile; gradient elution: 0-20 minutes, 10-95% B; 20-25 minutes, 95% B; 25-27 minutes, 95-10% B; 27-35 minutes, 10% B; flow rate: 8 mL/min; UV 200 nm. Collections at 22 minutes (Rt22.0) and 24 minutes (Rt24.0) showed bioactivity were named Peak 2 and Peak 3 (FIG. 1). After HPLC purification of the active flash fractions, bioactive compounds Peak 2 and Peak 3 were obtained from 15 L of the 1214-CHY4 culture using preparative HPLC.

Example 2. Use of 1214-CHY4 Peak 2, Peak 3, and 1214-CHY4 Crude Extract for Inhibiting Fish Pathogens An organism initially extracted from soil known as *Pseudomonas chlororaphis* subsp. *aurantiaca* 1214-CHY4 (1214-CHY4) was tested for its potential to limit the growth of fish pathogens (Table 1). 1214-CHY4 Peak 2, Peak 3, and 1214-CHY4 crude extract were tested. Fish pathogens were grown in their respective broth and temperature (Table 2) to exponential phase and diluted 1:5 in respective broth media in quadruplicate before starting the assay. Stock solution of 1214-CHY4 Peak 2, Peak 3, and 1214-CHY4 crude extract were made to 20 mg/mL using DMSO and then diluted with media to working concentrations (0.39, 0.78, 1.56, 3.13, 6.25, 12.5, 25, 50, 100, 200 μg/ml). In addition, a negative control (no compound, pathogen, DMSO, and media only), a compound control (compound and media, no pathogen), and a blank control (media, DMSO, and PBS only) were included. Control and blank solutions contained the equivalent to the highest volume of DMSO (0.4%). Following assay incubation times (Table 2), OD600 readings from each well were captured using a spectrophotometer to determine ΔOD600 for inference of MIC. The negative control and technical replicates of each concentration were combined and 100 μl plated on respective agar in triplicate to determine the final MLC. Two natural metabolites, 1214-CHY4 Peak 2 and Peak 3 were tested against nine aquatic pathogens for minimum inhibitory (MIC) and lethal (MLC) concentrations (Table 2). The same MICs were determined for Peak 2 and Peak 3 against *R. salmoninarum* (MIC=50 μg/mL), *S. iniae* (MIC=0.39 μg/mL), and *S. agalactiae* (MIC=6.25 μg/mL). However, only Peak 3 was lethal against the two species of *Streptococcus* tested here, with MLCs of 25 μg/mL and 50 μg/mL for *S. iniae* and *S. agalactiae*, respectively. When tested against four Gram-negative bacteria, 1214-CHY4 Peak 2 was efficacious against *T. maritimum* (MIC=3.13 μg/mL; MLC=200 μg/mL) and Peak 3 significantly reduced growth of *A. salmonicida* (MIC=100 μg/mL) and *V. parahaemolyticus* (MIC=1.56 μg/mL). Both 1214-CHY4 Peak 2 and Peak 3 inhibited the growth of *P. salmonis* (MIC=12.5 μg/mL) and *F. columnare* (MIC=0.5 μg/mL and 0.39 μg/mL, respectively). Reductions in growth were also observed for some Gram-negative bacteria, most promisingly for *T. maritimum* exposed to Peak 2. Furthermore, 1214-CHY4 crude extract was tested to limit the growth of four Gram-positive bacteria threatening salmon aquaculture (Table 3). Growth of *P. salmonis, R. salmoninarum, S. iniae*, and *S. agalactiae* was inhibited by 1214-CHY4, with minimum inhibitory concentrations 1.56 μg/ml, 100 μg/ml, 1.56 μg/ml, and 12.5 μg/ml, respectively. 1214-CHY4 crude extract was particularly efficacious in *P. salmonis, S. iniae*, and *S. agalactiae*, where lethal concentrations (25 μg/ml, 25 μg/ml, and 50 μg/ml, respectively) of the 1214-CHY4 crude extract were observed. Overall, 1214-CHY4 crude extract inhibited the growth of all pathogens tested, with lethal effects on three of the four.

TABLE 1

Disease, causative agent, geographical region, and economic losses for pathogens tested against *Pseudomonas chlororaphis* subsp. *aurantiaca* 1214-CHY4.

| Disease | Causative agent | Geographical region | Economic loss | References |
|---|---|---|---|---|
| Furunculosis | *A. salmonicida* | Ubiquitous - cold, marine, and freshwater | CAD 4 million/year | Boily et al., 2019; Nash et al., 2006 |
| Streptococcosis | *S. agalactiae, S. iniae* | Mexico, Africa, South America, Southeast Asia - warm water | USD 250 million/year for all *Streptococcus* sp. in tilapia; 40 million/year from *S. agalactiae* | Eto et al., 2020; Iregui et al., 2014 |
| Bacterial kidney disease | *R. salmoninarum* | Canada, Chile, Japan, USA, and most European countries | ca. 5 million globally[a] | Murray et al., 2011 |
| Columnaris | *F. columnare* | North and South America, Europe, Asia, Africa, and Australia | USD 30 million in U.S. | Shoemaker et al., 2011 |
| Tenacibaculosis | *T. maritimum* | Ubiquitous - cold water, marine environment | CAD 163 million/year in one British Columbia Farm | Wade and Weber, 2020 |

TABLE 1-continued

Disease, causative agent, geographical region, and economic losses
for pathogens tested against *Pseudomonas chlororaphis* subsp. *aurantiaca* 1214-CHY4.

| Disease | Causative agent | Geographical region | Economic loss | References |
|---|---|---|---|---|
| Acute hepatopancreatic necrosis disease | *V. parahaemolyticus* | Southeast Asia, China - warm water | USD 43 billion globally since discovery in 2009 | Kumar et al., 2021 |
| Saprolegniasis | *S. parasitica* | Ubiquitous in hatcheries - cold, fresh water | Estimated over USD 1 billion globally in all hosts | Lone and Manohar, 2018 |
| Piscirickettsiosis | *P. salmonis* | Chile, Canada, Norway, Ireland, and Scotland | Greatest economical loss in Chile (greater than 250 USD/year) | Rozas and Enríquez, 2014 |

TABLE 2

Minimum inhibitory concentration (MIC) and minimum
lethal concentration (MLC) for pathogens tested against
*Pseudomonas chlororaphis* subsp. *aurantiaca* 1214-CHY4 Peak 2 and Peak 3.

| Strain (related disease) | Medium/Temperature/ Assay incubation time | Minimum Inhibitory Concentration (µg/ml) | | Minimum Lethal Concentration (µg/ml) | |
|---|---|---|---|---|---|
| | | Peak 2 | Peak 3 | Peak 2 | Peak 3 |
| *Aeromonas salmonicida* | (TSA/TSB)/20° C./24 h | ND | 100 | ND | ND |
| *Streptococcus agalactiae* | (TSAY/TSBY)/28° C./48 h | 6.25 | 6.25 | ND | 50 |
| *Streptococcus iniae* | (TSAY/TSBY)/28° C./48 h | 0.39 | 0.39 | ND | 25 |
| *Vibrio parahaemolyticus* | (TSA2/TSB2)/37° C./24 h | ND | 1.56 | ND | ND |
| *Tenacibaculum maritimum* | (MA/MB)/15° C./8 days | 3.13 | ND | 200 | ND |
| *Saprolegnia parasitica* | GY/20° C./2 days | ND | ND | ND | ND |
| *Piscirickettsia salmonis* | L15/15° C./21 days | 12.5 | 12.5 | ND | ND |
| *Renibacterium salmoninarum* | KDM-2/15° C./14 days | 50 | 50 | ND | ND |
| *Flavobacterium columnare* | TYES/20° C./2 days | 0.5 | 0.39 | NA | NA |

ND - not determined
NA - not available

TABLE 3

Minimum inhibitory concentration (MIC) and minimum
lethal concentration (MLC) for pathogens tested against
*Pseudomonas chlororaphis* subsp. *aurantiaca* 1214-CHY4 crude extract

| Strain (related disease) | Medium/Temperature/ Assay incubation time | Minimum Inhibitory Concentration (µg/ml) | Minimum Lethal Concentration (µg/ml) |
|---|---|---|---|
| *Streptococcus agalactiae* | (TSAY/TSBY)/28° C./48 h | 12.5 | 50 |
| *Streptococcus iniae* | (TSAY/TSBY)/28° C./48 h | 1.56 | 25 |
| *Piscirickettsia salmonis* | L15/15° C./21 days | 1.56 | 25 |
| *Renibacterium salmoninarum* | KDM-2/15° C./14 days | 100 | ND |

ND - not determined

Example 3. Media Culture Compositions Used in the Examples

The media culture compositions used herein are presented in Table 4.

TABLE 4 includes exemplary media compositions used in the Examples.

| Medium Name | Composition | g per liter | Reference |
|---|---|---|---|
| YME | Yeast extract | 4.0 g | (Hamamoto et. al., 2015) |
| | Malt extract | 10 g | |
| | Glucose | 4.0 g | |
| | Tap water | 1.0 L | |
| L15 medium | L-15 MEDIUM LEIBOVITZ | 820 ml | (Leibovitz, 1963) |
| | Fetal bovine serum (FBS) | 150 ml | |
| | 100X Glutamax | 10 ml | |
| | 1M HEPES | 20 ml | |
| KDM-2 medium | Yeast extract | 10.0 g | (Matsui et al., 2009) |
| | Peptone | 0.5 g | |
| | L-cysteine | 1.0 g | |
| | Fetal bovine serum (FBS) –15% | 100 ml | |
| TSA/TSB | Tryptic soy broth | 30.0 g | (Ishiguro et al., 1981) |
| | Agar (TSA only) | 15.0 g | |
| TSAY/TSBY | Tryptic soy broth | 30.0 g | (Banu et al., 2010) |
| | Yeast extract | 5.0 g | |
| | Agar (TSAY only) | 15.0 g | |
| TSA2/TSB2 | Tryptic soy broth | 30.0 g | (Onarinde and Dixon, 2018) |
| | NaCl | 15.0 g | |
| | Agar (TSA2 only) | 15.0 g | |
| MA/MB | Marine broth | 37.4 g | (Mabrok et al., 2016) |
| | Agar (MA only) | 15.0 g | |
| TYES | Yeast extract | 0.4 g | (Holt et al., 1993) |
| | Tryptone | 4 g | |
| | $MgSO_4$ | 0.5 g | |
| | $CaCl_2$ | 0.5 g | |
| GY | Glucose | 10.9 g | (Eszterbauer et al., 2020) |
| | Yeast extract | 2.5 g | |
| | Agar | 15.0 g | |

Example 4. Bacterial Strains, Natural Products, and References Cited to Same

The bacterial strains and natural products described in this application and presented in the appended claims are well-known in the microbiology literature. These references are presented below in Table 5 for each of the cited bacterial strains and natural products disclosed herein, the contents of which are hereby incorporated by reference in their entirety.

TABLE 5

Bacterial strains, natural products and references cited in support as evidence of their availability.

| Bacterial Strains | Reference citation |
|---|---|
| *P. chlororaphis* subsp. *aurantiaca* 1214-CHY4 | Present disclosure |
| Natural Products | Reference citation |
| 1214-CHY4 crude extract | Present disclosure |
| 1214-CHY4 Peak 2 | Kato et al., 1993; Li et al., 2021; Pohanka et al., 2006 |
| 1214-CHY4 Peak 3 | Fuchs et al., 2013; Li et al., 2021 |

CITATIONS

Agnew, W. and Barnes, A. C. (2007). *Streptococcus iniae*: an aquatic pathogen of global veterinary significance and a challenging candidate for reliable vaccination. Vet Microbiol 122 (1-2): 1-15.

Alsina, M. and Blanch, A. R. (1993). First isolation of *Flexibacter maritimus* from cultivated turbot (*Scophthalmus maximus*). Bull Eur Assoc Fish Pathol 13:157-160

Amalina, N. Z., Santha, S., Zulperi, D., Amal, M. N. A., Yusof, M. T., Zamri-Saad, M., Ina-Salwany, M. Y. (2019). Prevalence, antimicrobial susceptibility and plasmid profiling of *Vibrio* spp. isolated from cultured groupers in Peninsular Malaysia. BMC Microbiol 11; 19(1):251.

Austin, B. and Austin, D. A. (2016). Bacterial fish pathogens: Disease of farmed and wild fish, 6th ed.; Springer: Cham, Switzerland, pp. 84-106.

Avendaño-Herrera, R. (2005) Avances en el conocimiento del patógeno de peces *Tenacibaculum maritimum*: implicaciones en el diagnóstico y prevención de la enfermedad. PhD thesis, Universidad de Santiago de Compostela Avendaño-Herrera, R., Frisch, A. E., Magariños, B. (2006). Tenacibaculosis infection in marine fish caused by *Tenacibaculum maritimum*: a review. Dis Aquat Organ 30; 71(3):255-66.

Banu, L., Conrads, G., Rehrauer, H., Hussain, H., Allan, E., van der Ploeg, J. R. (2010). The *Streptococcus mutans* serine/threonine kinase, PknB, regulates competence development, bacteriocin production, and cell wall metabolism. Infect Immun, 78: 2209-2220.

Bartholomew, J., Arkush, K. D., Soto, E. (2017). "*Piscirickettsia salmonis*". In Woo, P. T. K.; Cipriano, R. C. (eds.). Fish viruses and bacteria: pathobiology and protection. Wallingford: CABI. pp. 272-276.

Bebak, J. and Wagner, B. (2012). Use of Vaccination against Enteric Septicemia of Catfish and *Columnaris* Disease by the US Catfish Industry. J Aquat Anim Health 24, 30-36.

Bebak-Williams, J. and Bullock, G. L. (2002). Vaccination against furunculosis in arctic charr: efficacy of a commercial vaccine. J Aquat Anim Health 14:294-7.

Berg, A., Rodseth, O. M., Tangeras, A., Hansen, T. (2006). Time of vaccination influences development of adhesions, growth and spinal deformities in Atlantic salmon (*Salmo salar*). Dis Aquat Org 69,239-248, Boily, F., Malcolm, G., Johnson, S. C. (2019). Characterization of *Aeromonas salmonicida* and furunculosis to inform pathogen transfer risk assessments in British Columbia. DFO Can Sci Advis Sec Res Doc 2019/016 (October), vi+39 p.

Bravo, S. and Midtlyng, P. J. (2007). The use of fish vaccines in the Chilean salmon industry 1999-2003, Aquaculture 270 (1e4) 36e42.

Bravo, S. and Campos, M. (1989). Coho salmon syndrome in Chile. Fish Health Section, American Fisheries Society Newsletter. 17 (2): 3.

Brunt, J. and Austin, B. (2005). Use of a probiotic to control lactococcosis and streptococcosis in rainbow trout, *Oncorhynchus mykiss* (Walbaum). J Fish Dis 28 (12): 693-701.

Bullock, G., Hsu, T. C., Shotts, E. Jr. (1986). *Columnaris* Disease of Fishes. US Fish & Wildlife Publications. 129.

Cabello, F. C., Godfrey, H. P., Tomova, A., Ivanova, L., Dolz, H., Millanao, A., Buschmann, A. H. (2013). Antimicrobial use in aquaculture re-examined: its relevance to antimicrobial resistance and to animal and human health. Environ Microbiol 15, 1917-1942.

Camussetti, M., Gallardo, A., Aguilar, D., Larenas, J. (2015). Analisis de los costos por la utilizacion de quimioterapicos y vacunas en la salmonicultura. Salmonexpert 4, 46-49.

Charette, S. J. (2021). Microbe profile *Aeromonas salmonicida*: an opportunistic pathogen with multiple personalities. Microbiology (Reading). May; 167(5). doi: 10.1099/mic.0.001052.

Darwish, A. M., and Ismaiel A. A. (2003). Laboratory efficacy of amoxicillin for the control of *Streptococcus iniae* infection in sunshine bass. J Aquat Anim Health 15(3): 209-214.

Darwish, A. M., and Hobbs M. S. (2005). Laboratory efficacy of amoxicillin for the control of *Streptococcus iniae* infection in blue tilapia. J Aquat Anim Health 17(2): 197-202.

Declercq, A. M., Haesebrouck, F., Van den Broeck, W., Bossier, P., Decostere, A. (2013). *Columnaris* disease in fish: a review with emphasis on bacterium-host interactions. Vet Res 24; 44(1):27.

Durborrow, R. M., Thune, R. L., Hawke, J. P., Camus, A. C. (1988). *Columnaris* Disease—A Bacterial Infection Caused by *Flavobacterium columnare*. SRAC Publication (479).

Elliott, D. G., Pascho, R. J., Bullock, G. L. (1989). Developments in the control of bacterial kidney disease of salmonid fishes. Dis. Aquat. Org. 6, 201-215.

Eslamloo, K., Kumar, S., Caballero-Solares, A., Gnanagobal, H., Santander, J., Rise, M. L. (2020). Profiling the transcriptome response of Atlantic salmon head kidney to formalin-killed *Renibacterium salmoninarum*. Fish Shellfish Immunol. 98, 937-949.

Eszterbauer, E., Hardy, T., Rónai, Z, Sipos, D., Zsigmond, G. (2020) Cryopreservation of three *Saprolegnia* species (Oomycota): Preliminary evidence for the long-term archiving of water mould species, *Fungal Biol* 124: 682-687.

Eto, S. F., Fernandes, D. C., Moraes, A. C. De, Souza, P. G. De, Carvalho, A. De, Charlie-silva, I., Belo, M. A. A., Pizauro, J. M. (2020). Meningitis Caused by *Streptococcus agalactiae* in Nile Tilapia (*Oreochromis niloticus*): Infection and Inflammatory Response. Animals (Basel) 20; 10(11):2166.

Fairgrieve, W. T., Masada, C. L., McAuley, W. C., Peterson, M. E., Myers, M. S., Strom, M. S. (2005). Accumulation and clearance of orally administered erythromycin and its derivative, azithromycin, in juvenile fall Chinook salmon *Oncorhynchus tshawytscha*. Dis Aquat Organ 64, 99-106.

Flagg, T. A., Mahnken, C. V. M., Johnson, K. A. (1995). Captive broodstocks for recovery of Snake River sockeye salmon. In: Schramm H L, Piper R G (eds) Uses and effects of cultured fishes in aquatic ecosystems. Am Fish Soc Symp 15, Bethesda, MD, p 81-90

Florio, D., Gridelli, S., Fioravanti, M. L., Zanoni, R. G. (2016). First isolation of *Tenacibaculum maritimum* in a captive sand tiger shark (*Carcharias taurus*). J Zoo Wildl Med 47(1):351-3.

Frisch, K., Smage, S. B., Vallestad, C., Duesund, H., Brevik, Ø. J., Klevan, A., Olsen, R. H., Sjaatil, S. T., Gauthier, D., Brudeseth, B., Nylund, A. (2018). Experimental induction of mouthrot in Atlantic salmon smolts using *Tenacibaculum maritimum* from Western Canada. J Fish Dis 14.

Fryer, J. L., Hedrick, R. P. (2003). *Piscirickettsia salmonis*: a Gram-negative intracellular bacterial pathogen of fish. J Fish Dis. May; 26(5):251-62. doi: 10.1046/j.1365-2761.2003.00460.x.

Fryer, J. L., Lannan, C. N. (1993). The history and current status of *Renibacterium salmoninarum*, the causative agent of bacterial kidney disease in Pacific salmon. Fish Res 17:15-33.

Fuchs, S. W., Bozhüyük, K. A. J., Kresovic, D., Grundmann, F., Dill, V., Brachmann, A. O., Waterfield, N. R., Bode, H. B. (2013). Formation of 1,3-cyclohexanediones and resorcinols catalyzed by a widely occurring ketosynthase. Angew Chem Int Ed Engl 52(15), 4108-4112.

Gauthier J., Marquis H., Paquet V. E., Charette S. J., Levesque R. C., Derome N. (2021). Genomic Perspectives on *Aeromonas salmonicida* subsp. *salmonicida* Strain 890054 as a Model System for Pathogenicity Studies and Mitigation of Fish Infections. Front Mar Sci 1679(8).

Gobi, N., Malaikozhundan, B., Sekar, V., Shanthi, S., Vaseeharan, B., Jayakumar, R., Khudus Nazar, A. (2016). GFP tagged *Vibrio parahaemolyticus* Dahv2 infection and the protective effects of the probiotic *Bacillus licheniformis* Dahb1 on the growth, immune and antioxidant responses in *Pangasius hypophthalmus*. Fish Shellfish Immunol 52:230-8.

Gudding, R., Van Muiswinkel, W. B. (2013). A history of fish vaccination: Science-based disease prevention in aquaculture. Fish Shellfish Immunol. 35:1683-8.

Hamamoto, H., Urai, M., Ishii, K., Yasukawa, J., Paudel, A., Murai, M., Kaji, T., Kuranaga, T., Hamase, K., Katsu, T., Su, J., Adachi, T., Uchida, R., Tomoda, H., Yamada, M., Souma, M., Kurihara, H., Inoue, M., Sekimizu, K. (2015). Lysocin e is a new antibiotic that targets menaquinone in the bacterial membrane. Nat Chem Biol 11:127-133.

Henríquez, P., Kaiser, M., Bohle, H., Bustos, P., Mancilla, M. (2016). Comprehensive antibiotic susceptibility profiling of Chilean *Piscirickettsia salmonis* field isolates. J Fish Dis39(4):441-8.

Holt, R. A., Rohovec, J. S., Fryer, J. L. (1993) Bacterial cold-water disease. Bact Dis Fish 3-22.

Hoseinifar S. H., Sun Y-Z., Wang A., Zhou Z. (2018). Probiotics as Means of Diseases Control in Aquaculture, a Review of Current Knowledge and Future Perspectives. Front Microbiol 12; 9:2429

Hsu, H. M., Wooster, G. A., Bowser, P. R. (1994). Efficacy of enrofloxacin for the treatment of salmonids with bacterial kidney disease, caused by *Renibacterium salmoninarum*. J. Aquat Anim Health. 6, 220-223.

Iregui, C., Barato, P., Rey, A., Vasquez, G., Verjan, N. (2014). Epidemiology of *Streptococcus agalactiae* and Streptococcosis in Tilapia Fish. *Concept Press Ltd*, (January 2016), 18.

Ishiguro, E., Kay, W., Ainsworth, T., Chamberlain, J., Austen, R., Buckley, J., Trust, T. (1981). Loss of virulence during culture of *Aeromonas salmonicida* at high temperature. J Bacteriol 148(1):333-40.

Kato, S., Shindo, K., Kawai, H., Matsuoka, M., Mochizuki, J. (1993). Studies on free radical scavenging substances from microorganisms III. Isolation and structural elucidation of a novel free radical scavenger, resorstatin. J Antibiot 46(6), 1024-1026.

Koppang, E. O., Bjerkå's, I., Haugarvoll, E., Chan, E. K., Szabo, N. J., Ono, N., Akikusa, B., Jirillo, E., Poppe, T. T., Sveier, H., Tørud, B., Satoh, M. (2008). Vaccination-induced systemic autoimmunity in farmed Atlantic salmon. J Immunol 181, 4807-4814.

Kowalski, D. A., Drennan, D., Milano, V. M. (2018). Bacterial Kidney Disease Research.

Kumar, V., Roy, S., Behera, B. K., Bossier, P., & Das, B. K. (2021). Acute hepatopancreatic necrosis disease (Ahpnd):

Virulence, pathogenesis and mitigation strategies in Shrimp aquaculture. Toxins 13(8), 1-28.

Leibovitz, A. (1963). The growth and maintainance of tissue/cell cultures in free gas exchange with the atmosphere. Amer J Hyg 78:173-180.

Li, J., Shi, Y., Clark, B. R. (2021). Semi-synthesis of antibacterial dialkylresorcinol derivatives. J Antibiot 74, 70-75.

Lone, & Manohar. (2018). *Saprolegnia parasitica*, A lethal oomycete pathogen: Demands to be controlled. 24(2), 36-44

Mabrok, M., Machado, M., Serra, C. R., Afonso, A., Valente, L. M. P. and Costas, B. (2016). Tenacibaculosis induction in the Senegalese sole (*Solea senegalensis*) and studies of *Tenacibaculum maritimum* survival against host mucus and plasma. J Fish Dis 39: 1445-1455.

Matsui, T., Nishizawa T., Yoshimizu M. (2009). Modification of KDM-2 with culture-spent medium for isolation of *Renibacterium salmoninarum*. Fish Pathol 44, 139-144.

Miccoli, A., Saraceni, P. R., Scapigliati, G. (2019). Vaccines and immune protection of principal Mediterranean marine fish species. Fish Shellfish Immunol 94:800-809.

Midtlyng, P. J., Reitan, L. J., Speilberg, L. (1996). Experimental studies on the efficacy and side-effects of intraperitoneal vaccination of Atlantic salmon (*Salmo salar* L.) against furunculosis. Fish Shellfish Immun 6, 335-350.

Miranda, C. D., Godoy, F. A., Lee, M. R. (2018). Current status of the use of antibiotics and the antimicrobial resistance in the Chilean salmon farms. Front Microbiol 18; 9:1284.

Miranda, C. D., Tello, A., Keen, P. L. (2013). Mechanisms of antimicrobial resistance in finfish aquaculture environments. Front Microbiol 4, 233.

Mishra, A., Nam, G. H., Gim, J. A., Lee, H. E., Jo, A., Kim, H. S. (2018). Current challenges of *Streptococcus* infection and effective molecular, cellular, and environmental control methods in Aquaculture. Mol Cells 41, 495-505.

Murray, A. G., Munro, L. A., Wallace, I. S., Peeler, E. J., Thrush, M. A. (2011). Bacterial kidney disease: assessment of risk to Atlantic salmon farms from infection in trout farms and other sources. Scottish Marine and Freshwater Science 2 (3). http://www.scotland.gov.uk/Publications/2011/04/21144833/0 Edinburgh Navarrete, P., Mardones, P., Opazo, R., Espejo, R., Romero, J. (2008), Oxytetracycline Treatment Reduces Bacterial Diversity of Intestinal Microbiota of Atlantic Salmon. J Aquat Anim Health 20: 177-183

Nash, J. H. E., W. A., Findlay, C. C., Luebbert, O. L., Mykytczuk, S. J., Foote, E. N., Taboada, C. D., Carrillo, J. M., Boyd, D. J., Colquhoun, M. E., Reith, L. L. Brown. (2006). Comparative genomics profiling of clinical isolates of *Aeromonas salmonicida* using DNA microarrays. BMC Genomics 7:43.

Onarinde, B., and Dixon, R. (2018). Prospects for Biocontrol of *Vibrio parahaemolyticus* Contamination in Blue Mussels (*Mytilus edulus*)—A Year-Long Study. Front Microbiol 9, 1043.

Park, Y. K., Nho, S. W., Shin, G. W., Park, S. B., Jang, H. B., Cha, I. S., Ha, M. A., Kim, Y. R., Dalvi, R. S., Kang, B. J., et al. (2009). Antibiotic susceptibility and resistance of *Streptococcus iniae* and *Streptococcus parauberis* isolated from olive flounder (*Paralichthys olivaceus*). Vet Microbiol 136, 76-81.

Plumb, J. (1999). Health maintenance and principal microbial diseases of cultured fishes. Ames, IA: Iowa State University Press.

Plumb, J. A., and Hanson, L. A. (2011). Health maintenance and principal microbial diseases of cultured fishes. Hoboken, NJ: John Wiley & Sons.

Pohanka, A., Levenfors, J., & Broberg, A. (2006). Antimicrobial dialkylresorcinols from *Pseudomonas* sp. Ki19. Journal of Natural Products, 69(4), 654-657.

Powell, J., and Podlasly, T. (2015). *Tenacibaculum Maritimum*: Current knowledge and future directions. Campbell River: CAHS workshop.

Reyes-Becerril, M., Guluarte, C., Ceballos-Francisco, D., Angulo, C., Esteban, M. Á. (2017). Enhancing gilthead seabream immune status and protection against bacterial challenge by means of antigens derived from *Vibrio parahaemolyticus*. Fish Shellfish Immunol 60:205-218.

Rømer Villumsen, K., Dalsgaard, I., Holten-Andersen, L., Raida, M. K. (2012). Potential role of specific antibodies as important vaccine induced protective mechanism against *Aeromonas salmonicida* in Rainbow Trout. PLoS One 7, e46733.

Rozas, M. and Enriquez, R. (2014). Piscirickettsiosis and *Piscirickettsia salmonis* in fish: a review. J Fish Dis 37(3):163-88.

Rucker, R. R., Bernier, A. F., Whipple, W. J., Burrows, R. E. (1951). Sulfadiazine for kidney disease. Progress. Fish Culturist 13, 135-137.

Sakai, M. and Kobayashi, M. (1992). Detection of *Renibacterium salmoninarum*, the causative agent of bacterial kidney disease in salmonid fish, from pen-cultured coho salmon. Appl Environ Microbiol 58:1061-1063

Satoh, M., Bjerkå's, I., Haugarvoll, E., Chan, E. K., Szabo, N. J., Jirillo, E., Poppe, T. T., Sveier, H., Tørud, B., Koppang, E. O. (2011). Polyclonal hypergammaglobulinemia and autoantibody production induced by vaccination in farmed Atlantic salmon. Fish Shellfish Immun 30, 1080-1086.

Seghouani, H., Garcia-Rangel, C. E., Fuller, J., Gauthier, J., Derome, N. (2017). Walleye Autochthonous Bacteria as Promising Probiotic Candidates against *Flavobacterium columnare*. Front Microbiol. 18; 8:1349.

Sernapesca (2015). Informe Sanitario de Salmonicultura en Centros Marinos 2014. Servicio Nacional de Pesca y Acuicultura, https://www.sernapesca.cl/index.php?option=com_remository&Itemid=246&func=startdown&id=11083

Serrano, P. H. (2005). Responsible use of antibiotics in aquaculture. FAO Fish Tech Pap 469:1-97.

Shoemaker, C. A., Klesius, P. H., Drennan, J. D., Evans, J. J. (2011). Efficacy of a modified live *Flavobacterium columnare* vaccine in fish. Fish Shellfish Immunol 30, 304-308.

Soliman, W. S., Shaapan, R. M., Mohamed, L. A., Gayed, S. S. R. (2019). Recent biocontrol measures for fish bacterial diseases, in particular to probiotics, bio-encapsulated vaccines, and phage therapy. Open Vet J. 9(3): 190-195.

Soltani, M., Shanker, S., Munday, B. L. (1995). Chemotherapy of Cytophaga/*Flexibacter*-like bacteria (CFLB) infections in fish: studies validating clinical efficacies of selected antimicrobials. J Fish Dis 18:555-565

Stoffregen, D. A., Backman, S. C., Perham, R. E., Bowser, P. R., Babish, J. G. (1996). Initial disease report of *Streptococcus iniae* infection in hybrid striped (sunshine) bass and successful therapeutic intervention with the fluoroquinolone antibacterial enrofloxacin. J World Aquac Soc 27(4): 420-434.

Tang, K. F. J., Bondad-Reantaso, M. G. (2019). Impacts of acute hepatopancreatic necrosis disease on commercial shrimp aquaculture. Rev Sci Tech 38(2):477-490

Toranzo, A. E., Magari~nos, B., Romalde, J. L. (2005). A review of the main bacterial fish diseases in mariculture systems. Aquaculture, 246, 37-61.

Toranzo, A. E., Santos, Y., Bandin, I., Romalde, J. L., Ledo, A., Fouz, B., Barja, J. L. (1990). Five year survey of bacterial fish infections in continental and marine aquaculture in northwest Spain. World Aquacult 21:91-94 van Gelderen, R., Carson, J., Nowak, B. (2009). Vaccination of Atlantic salmon (*Salmo salar* L.) against marine flexibacteriosis. Aquaculture 288, 7-13.

Villumsen, K. R., Koppang, E. O., Raida, M. K. (2015). Adverse and long-term protective effects following oil-adjuvanted vaccination against *Aeromonas salmonicida* in rainbow trout. Fish Shellfish Immun 42, 193-203.

Wade, J., and Weber, L. (2020). Characterization of *Tenacibaculum maritimum* and mouthrot to inform pathogen transfer risk assessments in British Columbia. (November). Retrieved from http://www.dfo-mpo.gc.ca/csas-sccs/

Wiens, G. D. (2011). Bacterial Kidney Disease (*Renibacterium salmoninarum*), Fish Diseases and Disorders: Viral, Bacterial and Fungal Infections, 2nd ed.; Woo, P. T. K., Bruno, D. W., Eds.; CAB International: Wallingford, UK, pp. 338-374.

Wise, A. L., LaFrentz, B. R., Kelly, A. M., Khoo, L. H., Xu, T., Liles, M. R., Bruce, T. J. (2021). A Review of bacterial co-infections in farmed catfish: Components, Diagnostics, and Treatment Directions. Animals (Basel). 12; 11(11): 3240.

Zhou, T., Yuan, Z., Tan, S., Jin, Y., Yang, Y., Shi, H., Wang, W., Niu, D., Gao, L., Jiang, W., Gao, D., Liu, Z. (2018). A review of molecular responses of catfish to bacterial diseases and abiotic stresses. Front. Physiol 9, 1113.

INCORPORATION BY REFERENCE

All literature, publications, patents, patent applications, and related material cited here are incorporated by reference as if fully set forth herein.

What is claimed is:

1. A method of controlling a fish pathogen and an associated disease of a fish, comprising:
producing an aquacultural composition from *P. chlororaphis* subsp. *aurantiaca* 1214-CHY4 of ATCC Accession No. PTA-126941, said aquacultural composition comprising Formula (I), Formula (II), or a combination thereof:

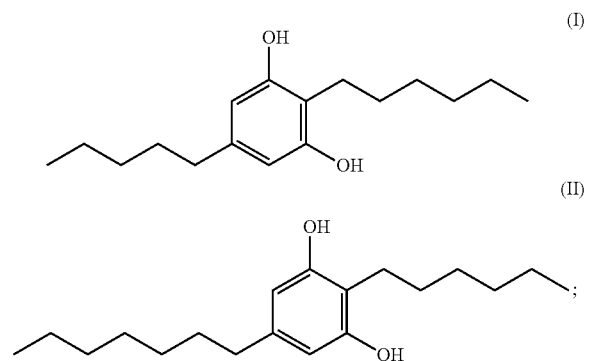

and
applying said aquacultural composition to the fish to inhibit the growth of the fish pathogen and the associated disease on the fish.

2. The method of claim 1, wherein the fish pathogen is selected from the group consisting of *Streptococcus agalactiae*, *Streptococcus* iniae, *Renibacterium salmoninarum*, *Aeromonas salmonicida*, *Tenacibaculum maritimum*, *Vibrio parahaemolyticus*, *Piscirickettsia salmonis*, *Flavobacterium psychrophilum* and *Flavobacterium columnare*.

3. The method of claim 1, wherein the associated disease is selected from the group consisting of streptococcosis, bacterial kidney disease, furunculosis, tenacibaculosis, vibriosis, piscirickettsiosis, and *columnaris* diseases.

4. The method of claim 1, wherein the fish is selected from the group consisting of salmonids, trout, cyprinids, pikes, perches, bullheads, turbots, halibuts, catfish, goldfish, eel, tilapia, carps, freshwater aquarium fish, fresh-water fish, sea-water fish, wild fish, and farm fish.

5. A method of controlling a fish pathogen disease, comprising: applying an aquacultural composition comprising between about $1.0 \times 10^5$ and $1.0 \times 10^9$ cfu per mL or $1.0 \times 10^5$ and $1.0 \times 10^9$ cfu per gram with a carrier of *P. chlororaphis* subsp. *aurantiaca* 1214-CHY4 of ATCC Accession No. PTA-126941 to fish to inhibit the growth of a fish pathogen and an associated disease.

6. The method of claim 5, wherein applying an aquacultural composition to the fish is administered by at least one of following methods: a food-borne oral route, bioencapsulation, bath, dip, flush, injection, or topical application.

7. The method of claim 5, wherein the aquacultural composition is selected from spent media or natural metabolites of *P. chlororaphis* subsp. *aurantiaca* 1214-CHY4 of ATCC Accession No. PTA-126941, a composition comprising of the Formula (I) isolated from *P. chlororaphis* subsp. *aurantiaca* 1214-CHY4 of ATCC Accession No. PTA-126941:

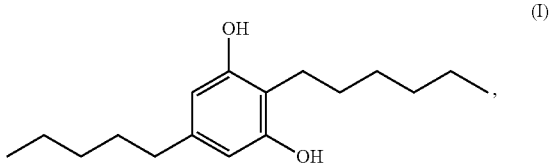 [SMILES: CCCCCCc1c(O)cc(CCCCC)cc1O]

a composition comprising of the Formula (II) isolated from *P. chlororaphis* subsp. *aurantiaca* 1214-CHY4 of ATCC Accession No. PTA-126941:

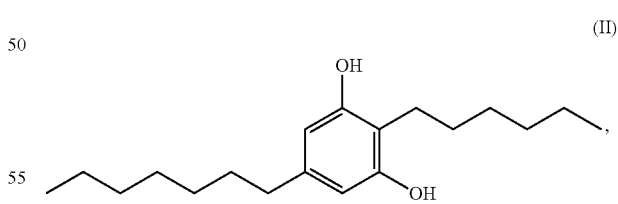

or a combination thereof.

8. The method of claim 5, wherein the composition comprising between about $5.0 \times 10^7$ and $2.0 \times 10^8$ cfu per mL or about $5.0 \times 10^7$ and $2.0 \times 10^8$ cfu per gram with a carrier of *P. chlororaphis* subsp. *aurantiaca* 1214-CHY4 of ATCC Accession No. PTA-126941.

9. The method of claim 5, wherein the fish pathogen is selected from the group consisting of *Streptococcus agalactiae*, *Streptococcus* iniae, *Renibacterium salmoninarum*, *Aeromonas salmonicida*, *Tenacibaculum maritimum*, *Vibrio*

*parahaemolyticus, Piscirickettsia salmonis, Flavobacterium psychrophilum* and *Flavobacterium columnare*.

10. The method of claim 5, wherein the associated disease is selected from the group consisting of streptococcosis, bacterial kidney disease, furunculosis, tenacibaculosis, vibriosis, piscirickettsiosis, and *columnaris* diseases.

11. The method of claim 5, wherein the fish is selected from the group consisting of salmonids, trout, cyprinids, pikes, perches, bullheads, turbots, halibuts, catfish, goldfish, eel, tilapia, carps, freshwater aquarium fish, fresh-water fish, sea-water fish, wild fish, and farm fish.

\* \* \* \* \*